United States Patent
Arocha (10) Patent No.: US 9,877,799 B2
(45) Date of Patent: Jan. 30, 2018

(54) REGULATED PERIODONTAL DISPENSING APPARATUS AND MULTIPLE DOSE APPLICATOR WITH A SEMILUNAR VALVE

(75) Inventor: Max Arocha, Plantation, FL (US)

(73) Assignee: PharmaPhD, Inc., Plantation, FL (US)

( * ) Notice: Subject to any disclaimer, the term of this patent is extended or adjusted under 35 U.S.C. 154(b) by 453 days.

(21) Appl. No.: 14/382,740

(22) PCT Filed: Jun. 11, 2012

(86) PCT No.: PCT/US2012/041837
§ 371 (c)(1),
(2), (4) Date: Sep. 3, 2014

(87) PCT Pub. No.: WO2012/170986
PCT Pub. Date: Dec. 13, 2012

(65) Prior Publication Data
US 2015/0017602 A1    Jan. 15, 2015

Related U.S. Application Data

(60) Provisional application No. 61/495,425, filed on Jun. 10, 2011.

(51) Int. Cl.
*A61C 1/08* (2006.01)
*A61C 19/06* (2006.01)
*A61C 5/62* (2017.01)

(52) U.S. Cl.
CPC ............... *A61C 1/087* (2013.01); *A61C 5/62* (2017.02); *A61C 19/063* (2013.01)

(58) Field of Classification Search
CPC . A61C 5/04; A61C 17/00; A61C 3/02; A61M 11/00; A61M 11/02; A61M 5/31

USPC .............................................. 433/83, 89, 90
See application file for complete search history.

(56) References Cited

U.S. PATENT DOCUMENTS

| | | | | |
|---|---|---|---|---|
| 4,444,560 A | * | 4/1984 | Jacklich | A61M 5/31595 222/391 |
| 5,389,585 A | * | 2/1995 | Konig | B01J 12/02 501/152 |
| 5,609,601 A | * | 3/1997 | Kolesa | A61B 17/29 606/170 |
| 5,673,686 A | * | 10/1997 | Villax | A61M 15/0028 128/203.12 |
| 5,743,436 A | * | 4/1998 | Wilcox | A61C 5/064 222/137 |
| 5,778,873 A | * | 7/1998 | Braithwaite | A61M 15/0045 128/203.15 |
| 6,095,814 A | * | 8/2000 | Petrich | A61C 5/062 222/137 |
| 7,976,489 B2 | * | 7/2011 | Lawter | A61C 5/062 604/63 |

(Continued)

*Primary Examiner* — Nicholas Lucchesi
(74) *Attorney, Agent, or Firm* — Ted W. Whitlock (57) ABSTRACT

The present invention is a hand-held device for dispensing multiple controlled dosage of powered material having a main body, a cavity in the main body constructed and arranged to be operatively associated with an actuator for dispensing a medicament, an actuator constructed and arranged for dispensing said medicament from said cavity through a delivery device, and a tip attached to said second end of said main body, wherein said tip is constructed and arranged at a fixed angle relative to said main body to facilitate periodontal delivery of a medicament.

5 Claims, 9 Drawing Sheets

( FIG.5 )

(56) References Cited

U.S. PATENT DOCUMENTS

| | | | |
|---|---|---|---|
| 7,976,490 B2 * | 7/2011 | Lawter | A61M 37/0069 604/63 |
| 2004/0258625 A1 * | 12/2004 | Nilsson | A61M 15/0045 424/46 |
| 2007/0101991 A1 * | 5/2007 | Myrman | A61M 15/0028 128/203.15 |
| 2009/0142728 A1 * | 6/2009 | Lawter | A61J 7/0053 433/89 |
| 2009/0171147 A1 * | 7/2009 | Lee | A61B 17/29 600/104 |
| 2011/0054418 A1 * | 3/2011 | Pugh | A61F 9/00772 604/285 |

* cited by examiner

FIG.5
(SECTION E-E OF FIG.4)

REGULATED PERIODONTAL DISPENSING APPARATUS AND MULTIPLE DOSE APPLICATOR WITH A SEMILUNAR VALVE

INDEX TO RELATED APPLICATIONS

This application is a National Stage Application under 35 USC 371 of PCT/US12/41837 which claims benefit to U.S. Provisional Patent Application Ser. No. 61/495,425 filed Jun. 10, 2011, the disclosures of which are incorporated herein by reference in their entirety.

BACKGROUND OF THE INVENTION

Field of the Invention

Dental dispensers for delivering medicated powder to the interface of the gum and tooth are commonly used by dentists and dental health professionals. Although devices exist and are used on a large commercial scale, dental practitioners often use the commercial devices and accept the undesired deficiencies regarding ease of use and efficacy.

Typically, theses are provided as single dose delivery devices whereby after each dose a pre-filled tip is removed and replaced and a subsequent dose is given. There are numerous deficiencies with conventional delivery devices. A first deficiency relates to the amount of pressure required to actuate a spring-loaded device in order to effectuate delivery. Another deficiency relates to patients requiring multiple doses of a medicated powder, which require the dental health professional to repeatedly, change a pre-filled tip. The present invention has addressed these deficiencies by providing a delivery device that has an adjustable actuator and is constructed and arranged to deliver multiple doses.

SUMMARY OF THE INVENTION

A problem associated with currently used powered multi-dose dispenser for periodontal powder does not exist. The only multi-dose devices are for liquids. When using a multi-dose apparatus for powders, it is difficult to effectively seal the apex of applicator to prevent forward movement of the power and to keep the next power dose dry from the oral cavity fluids and moisture. It is a prime object of this invention to overcome this disadvantage.

In one embodiment, the device is constructed and arranged so as to protect the loaded tip applicator orifice from fluids coming entering therein. This is done by placing a latex (or a latex alternative also for patient allergic to latex) type of valve at the end of the applicator orifice or some form of perforated latex valve. Thus, at least partially sealing off the tip applicator orifice with a latex membrane and then puncture the membrane in the middle so the power can only come out of the tip when pressure is apply upon pressing on the rotating paddle.

Multiple doses are one advantage of the present invention. Other advantages include, but are not limited to the configuration and the controlled pressure in which multiple doses, for example, 1 mg doses of minocycline would be expelled into the periodontal pocket upon pressing an actuator. In one embodiment, the actuator is a rotating paddle.

The present invention improves upon prior devices in, at least the following:
a. the dispensing apparatus is for multiple dose application.
b. the apparatus does not have a syringe design; therefore it is better suited for patient afraid of syringes.
c. prior devices do not control the pressure in which the dry powered exits the cartridge. The problem with this is that in a deep periodontal pocket the powered medication may not reach the bottom of the pocket if proper pressure is not applied with the conventional devices. In the present invention, the apparatus would be adjusted and calibrated to improve delivery
by controlling the pressure in which the dry powered exits the applicator tip.

A device for the treatment of periodontal disease includes an ergonomic body that has a "pen-style" configuration, a reset internal ratchet mechanism, a paddle and a loaded blunt tip applicator that is locked into the body when use. The multiple dose blunt-tipped and elliptical end applicator penetrates into periodontal pockets space for direct application of the periodontal therapeutic powered agent.

Exact dosage of dry periodontal therapeutic powered is extremely important when efficient periodontal topical therapeutics means are used to treat periodontal disease. In this invention, such dosing is provided by providing for the structure of a regulated (control) dispenser, having a design in which applicator with a plunger inside interact with ratchet and pawl mechanism in inside the body for fixed movement of the plunger.

This regulated dispensing apparatus and method improve on the contemporary art of single dose periodontal power syringe application by providing a dispensing apparatus that can effectively deliver regulated multiple dosing powdered periodontal therapeutic microcapsules directly into more than one periodontal pocket site. This ergonomic "pen-style" design also improves maneuverability.

The body of dispensing apparatus, in one embodiment is cylinder having a hollow interior cavity and has inside ratchet teeth, a plunger and a stopper pawl. The stopper pawl prevents return movement of the plunger. A plunger has ratchet teeth. The stopper pawl and the plunger possibly interacting with each other to deliver with precision and uniformity a medicament in a pharmaceutically acceptable manner.

In one embodiment, the regulated multi-dose applicator is in the shape of a hollow thin conical elliptical shape at the apex with an approximately 45-degree angle. The apex from this assisting device penetrates under the periodontal pocket between the gingiva (gum line) and the tooth. This allows the applicator tip to expel the powered periodontal therapeutic medication into the gingiva crevice (gums pocket) upon pressing the paddle with index finger. The applicator tip may have a dosage scale. The body paddle structure permit to expel power by, for example, 1 mg, and exact dose, corresponding to each pressing on the paddle. Further, each click sound may represent 1 mg microcapsule dose application.

Applicator holds a plurality of doses, for example, a total of 4 mg multi-dose to be dispensed at 1 mg dry powered microcapsule minocycline per periodontal site.

It is contemplated that the invention has a significant role in the future of multi-dose application of periodontal powered agents that are placed locally into the gums pockets in a control fashion. The closest analogue to the invention is high-pressure syringe with pressure indicator for periodontal ligament injection.

The periodontal multidose apparatus of the present invention is for the dispensing of a power 1 mg microparticle per periodontal pocket. The semilunar latex free valve at the end of the applicator tip is to keep microparticles dry, give resistance to the expulse of the power and keep power somewhat wrapped. The latex free valve may be a semilunar shape or other shapes.

A typical problem associated with this type of powered multi-dose dispenser may be that it is difficult to effectively seal the apex of applicator to prevent forward movement of the power and to keep the next power dose dry from the oral cavity fluids and moisture. It is a prime object of this invention to overcome this disadvantage.

In one embodiment, the apparatus of the present invention includes a reusable having body ratchet mechanism that is fitted with a multidose disposable applicator loaded with premixed periodontal therapeutic powered agent.

The present invention will appeal to dental practitioners because the ergonomic periodontal dispenser puts optimal multiple (1 mg minocycline microcapsules) dosing control at their fingertips.

This invention allows the following:
Allows for multiple sites applications of powered antibiotics;
Reduces the amount of disposable instrumentation;
Control dosing;
Multiple dose to make it easy to treat multiple sites on the same patient and avoiding reloading;
Angled tip applicator to improves access to injection delivery site;
The semilunar from the valve tip applicator to keep powered agent dry between sites application;
Ergonomic design to be easy to use and comfortable to hold
Delivers of a precise 1 mg powered minocycline;
High tactile and well-balanced design to permit a controlled delivery with each click from the activator paddle;
Support of the index finger to give optimal control;
Ease to activate the dispenser "paddle" without straining
Substantially different from a syringe (Feasible for patient afraid of syringes);
Solid plastic material to be "safe" in the mouth and withstand common methods of eliminating bacteria;
Reusable (fully auto-clavable) (Sterilizable);
Lightweight and ergonomic;

This device is for use in conjunction with all periodontal treatments including, but not limited to, powered, time-release, periodontal medication, with a view to develop a multiple dosage delivery associated with conditional applicators for such medication.

The newer time released medications will most likely continue to be packaged and applied by cartridge/syringe. Therefore, it is contemplated that the invention as disclosed herein will play a significant role in the future application of pressure control multiple dosage medications, time-release, that are placed locally into the gingiva crevice (periodontal pocket) for the treatment of periodontal disease.

This invention also plays a significant role in assisting in the placement of sub-gingival, locally placed powered, time-release, periodontal medications.

The present invention provides a hand-held device useful for dispensing multiple controlled dosage of powered material. (It is controlled in two aspects: Amount and delivery force). For the amount: we are only dispensing 1 mg of powered minocycline at a time per "click" sound upon pressing on the rotating paddle. For the delivery force: we may calibrate the apparatus to deliver x amount of Newton per square centimeter upon pressing on the rotating paddle.

In one embodiment, a pen style or shaped powder dispenser capable of delivering multiple control dosage powered agents under x Newton per square centimeter for use in the treatment of periodontal disease. The amount is varied depending on the device.

The invention provides an article and method for delivery of multiple controlled dosages of powered agents to be delivery into periodontal pockets encompassing the devices described herein.

In one embodiment, the present invention is a hand-held device for dispensing multiple controlled dosage of powered material comprising:
a main body having a first end and a second end;
a cavity within the main body, said cavity constructed and arranged to be operatively associated with an actuator for dispensing a medicament;
an actuator constructed and arranged for dispensing said medicament from said cavity through a delivery device;
a tip attached to said second end of said main body, wherein said tip is constructed and arranged at a fixed angle relative to said main body to facilitate periodontal delivery of said medicament.

The device is constructed and arranged to provide delivery of a plurality of doses of said medicament. The multiple dose delivery is accomplished in a manner that will deliver distinct and precise does of a medicament with each actuation of the device. As generally understood, the actuator does not directly deliver the medicament, the actuator initiates a mechanism by which physical delivery of the dose occurs.

The device provides pharmaceutically acceptable precision and uniformity to delivery of said medicament from said device. The terms precision and uniformity are as commonly known in the art and can include delivery of an amount having a variance of +/−10%, +/−8%, +/−5%, and/or +/−3%.

In one embodiment, the device has a premixed periodontal therapeutic powered agent and contains at least one series having a first medicament dose, an inert material and second medicament dose, wherein an initial actuation of said device delivers said first medicament dose and a subsequent actuation delivers said second medicament dose.

The inert material divides the powder into individualized doses and serves as a moisture barrier against moisture contacting the second dose while the first dose is applied. In practical terms, when the tip of the article is placed along the periodontal surface (e.g. between the tooth and the gum) moisture is present. Once the dose is delivered, there is moisture around the delivery tip. If moisture were to contact a subsequent dose of medicament, the moisture would interfere with the delivery of a subsequent dose. Thus, the present invention provides for a series having medicament, inert material, and medicament in order to protect doses to be delivered after the initial dose. Although as described herein there are 2 doses, this is for illustrative purposes only. The device can be constructed and arranged with more than 2 doses. In one embodiment, the configuration has 2-4 doses in a single device.

Thus the placement of the inert material prevents moisture from contacting a dose subsequent to the initial dose and facilitates precise delivery of individual medicament doses.

In one embodiment, the device multi-dose applicator is an applicator tip containing prefilled and pre measured doses of a medicament. If there is more than one dose in the applicator tip, each dose is separated by an inert material.

In one embodiment, the multi-dose applicator is a reservoir having individualized doses that are retrieved and positioned for delivery upon actuation. For analogy, this is contemplated to be a mechanism similar to a conventional manual coin changer as are well known such as, devices available at http://www.moneymachines.com/beltchanger.html the disclosure of which is incorporated herein by reference.

The manual fare or coin changer/collection device is the coin dispenser, distributed by Jacques L. Galef. Mounted either in a driver's cab or on the belt of a conductor, the coin dispenser usually takes the form of a number of tubes fitted in a line together. Each tube holds a different denomination and tends to have some sort of trigger which will release the coin from the bottom. The trigger has a mechanism that provides individual discharge of coins.

In a similar fashion, a plurality of doses, separated by inert material, are individually dispensed from a tube or other cavity and subsequently delivered for periodontal therapy using the device of the present invention.

In a preferred embodiment, the force of delivery is user adjustable. That is to say, the amount of pressure applied to the actuator is user adjustable and can be made more or less sensitive based on user preference. The adjustable pressure of actuation is independent of delivery. The device is formed such that any actuation provides a precise and reproducible amount of medicament delivered.

In one embodiment, the delivery device is a regulated multi-dose applicator in the shape of a hollow thin conical elliptical shape at it's apex, wherein said applicator in constructed having an approximately 10-50 degree angle offset from a longitudinal line through the center of the device.

In one embodiment, it is contemplated that the tip is a non-tapered tip. In this embodiment, the portion of the tip inserted into the area for periodontal treatment, has a constant outer diameter for 0.01-2.00 mm distance along the tip in the direction from opening 62 towards main body 12. It is contemplated that a constant outer diameter provides increased control of delivery over tapered tip devices.

BRIEF DESCRIPTION OF THE SEVERAL VIEWS OF THE DRAWING

FIG. 11 is a sectional view of FIG. 13 showing the applicator tip with connector and single outer shot.

DETAILED DESCRIPTION OF THE PREFERRED EMBODIMENT

Figure 1:
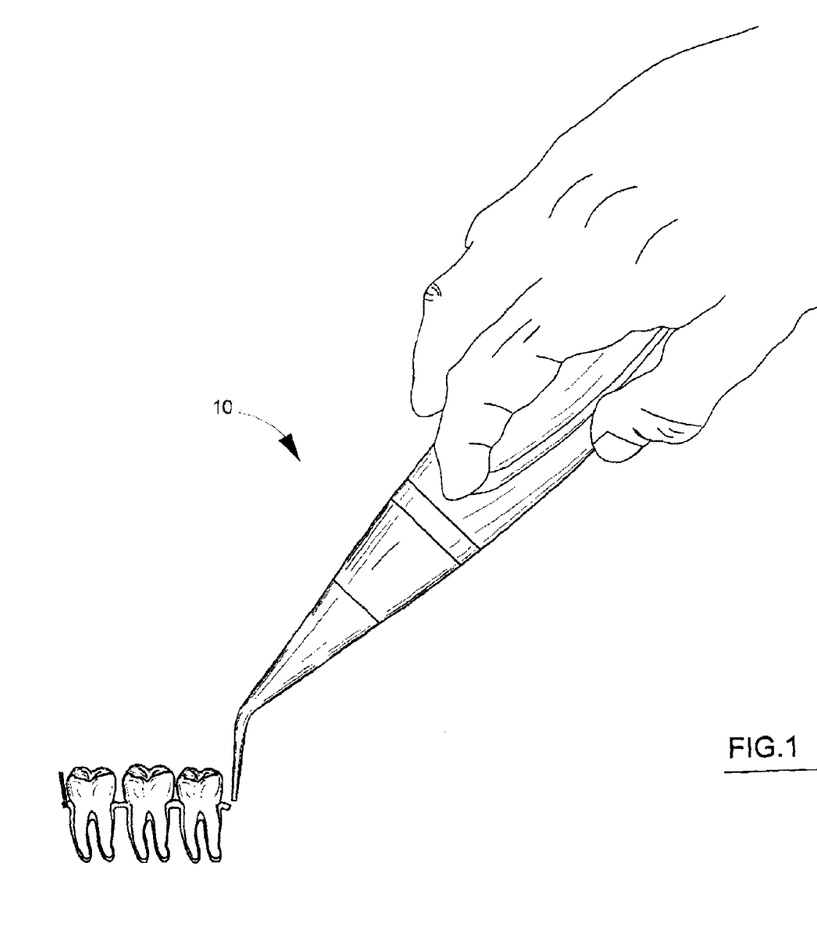
FIG. 1 is a perspective view of the powder dispenser of the present invention shown hand held in environment of use.
Figure 2:
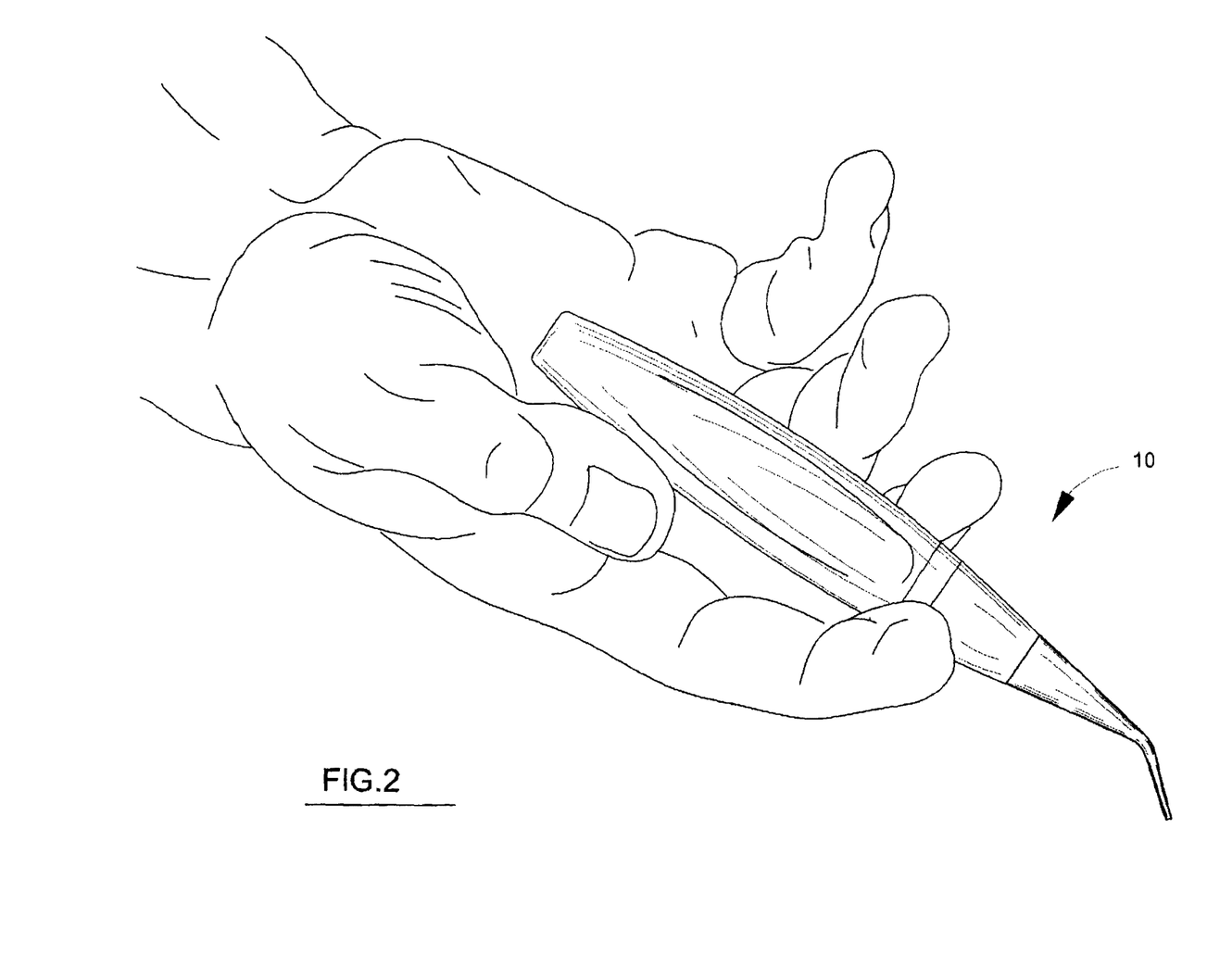
FIG. 2 is as a bottom view of the dispenser of the present invention held in a hand.
Figure 3:
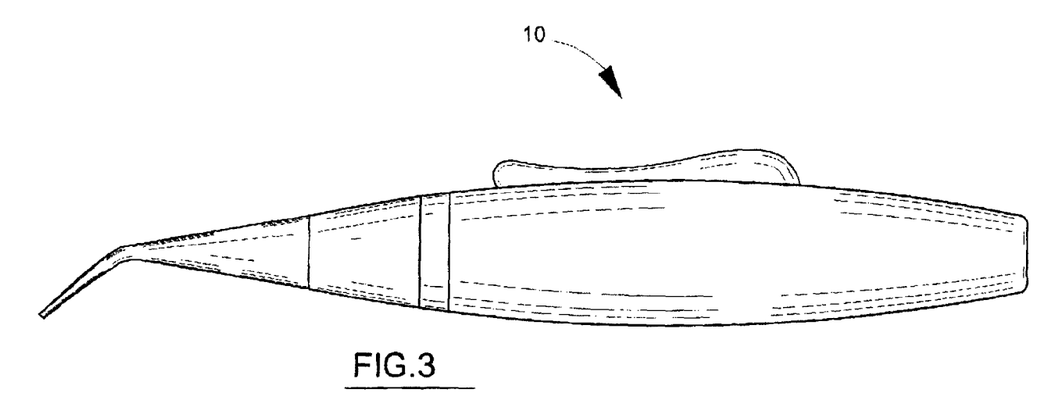
FIG. 3 is a side view of the powder dispenser of the present invention.
Figure 4:
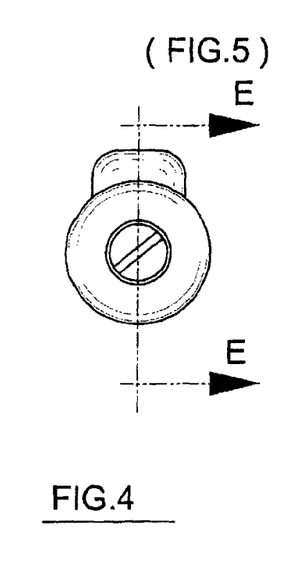
FIG. 4 is an end view of the present invention.
Figure 5:
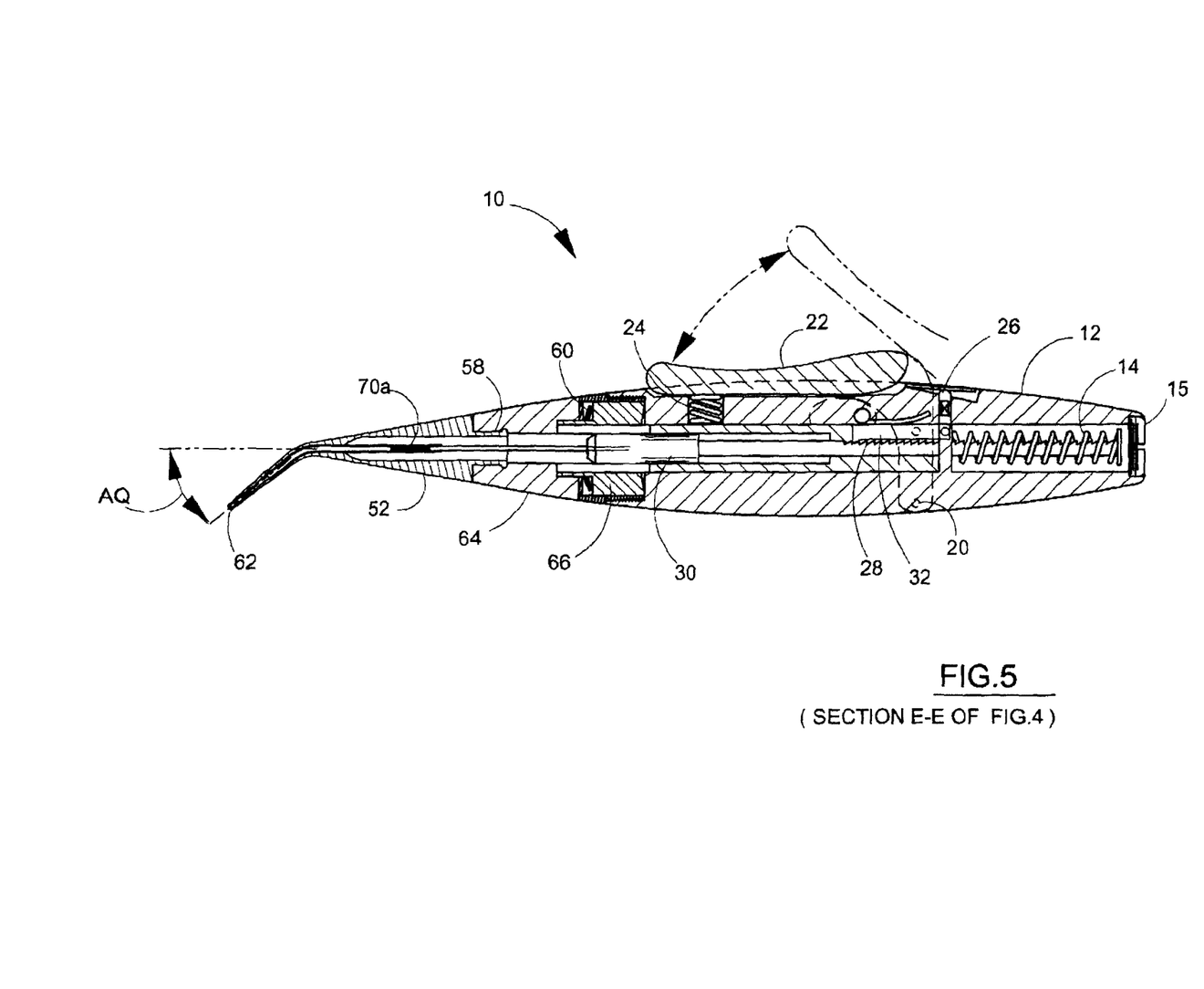
FIG. 5 is a section view along section lines E-E of the FIG. 4.
Figure 6:
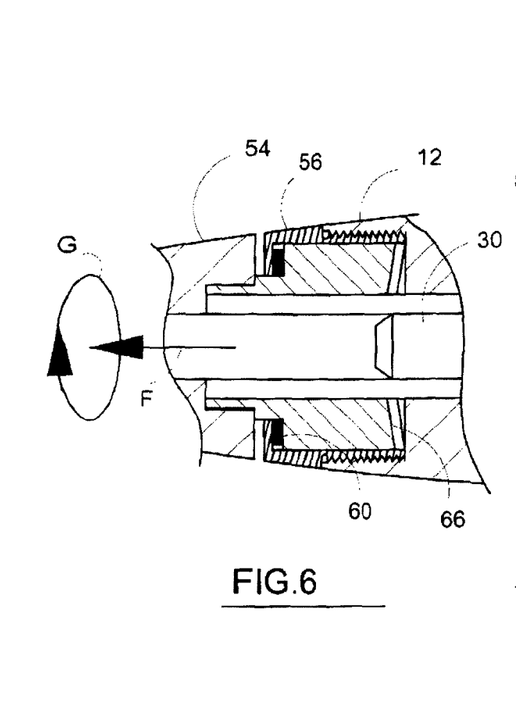
FIG. 6 is an enlarged sectional view of the ratchet positioning components shown in the open or rotational position.

The present invention provides a multi dose hand held oral medicinal powder dispenser. Dispenser 10 is constructed and arranged to deliver oral medicated powder to the interface of teeth and gums as is known in the art and depicted in FIG. 1. This device provides delivery of periodontal medicaments. Dispenser 10 represents numerous significant improvements over prior articles. Dispenser 10 has an actuator 22 which is user adjustable such that a selected amount of pressure will cause dispenser 10 to eject medicament from exit 62 of tip assembly 52. As best seen in FIG. 5 a cross-section of article 10 of the present invention actuator 22 is pivotably attached at actuating arm pivot 20. Actuator 22 raises up pivotably in an angular fashion and down toward body surface 12 of article 10 as shown by directional arrows in FIG. 5 demonstrating movement of actuator 22. Enclosed on a first end of article 10 is rack spring 14 which urges from end cap 15 inward towards the center of the article and in the ultimate direction of exit 62 of tip assembly 52. End cap 15 is removable and provides access to the internal elements of article 10 contained within body 12. The mechanism controls plunger 30 which is operatively associated with tip assembly 50 whereby medical powder 70 is forced through tip assembly 50 and exists the apparatus through exit orifice 62.

In the embodiment shown the distance plunger 30 travels is fixed by interaction with rack 28 and plunger shot feed 30. Rack 28 interacts with pawl 32 and provided for fixed movement of plunger 30 based on the distance and angular pitch between teeth on rack 28. This ensures precision of delivery as would be required in the delivery of medicaments in precise amounts with a pharmaceutically acceptable degree of variation. A pharmaceutically acceptable variation is subject to change due to regulatory considerations but in one embodiment is +/−10%. In a preferred embodiment, it is +/−8%. In a more preferred embodiment it is +/−5%. As contemplated, the delivery is also capable of delivery with precision of +/−3%.

Figure 12:
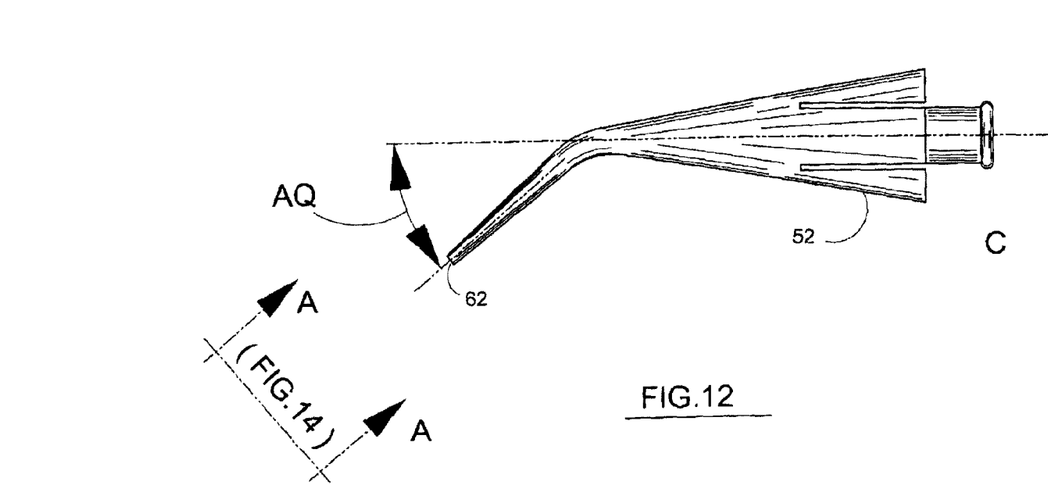
FIG. 12 is a side view of the applicator tip.
Figure 13:
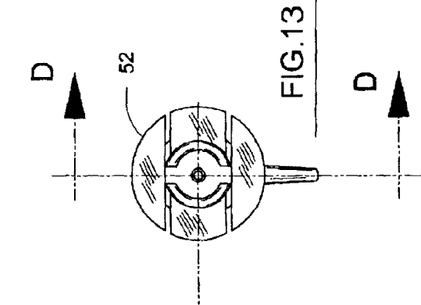

The present invention further comprises an improvement whereby a rotatable ratchet head 66 rotate applicator tip assembly 52. Thus when a dentist or other health professional is in need of manipulating the ultimate position of applicator tip 52 rather than rotating the entire body, which will also require rotating the actuator 22 in a position that could be in a sub-optimal orientation, rotation of ratchet head 66 will ultimately rotate applicator 52 into a desired position while actuator 22 remains in an optimal position for use. Simply put, the tip rotates along with the tip assembly and the remainder of the device does not require rotation. A preferred embodiment provides a fixed angle of the termination of applicator tip 52 at exit 62. As best seen in FIG. 12, tip assembly 52 is formed with a permanent angle designated by dimension AQ which ranges from 10-50 degrees. In preferred embodiments, angle AQ is 15-45 degrees. In another preferred embodiment is 25-45 degrees. In another preferred embodiment is 30-45 degrees. In another preferred embodiment is 35-45 degrees. In another preferred embodiment is 40-45 degrees.

Figure 7:
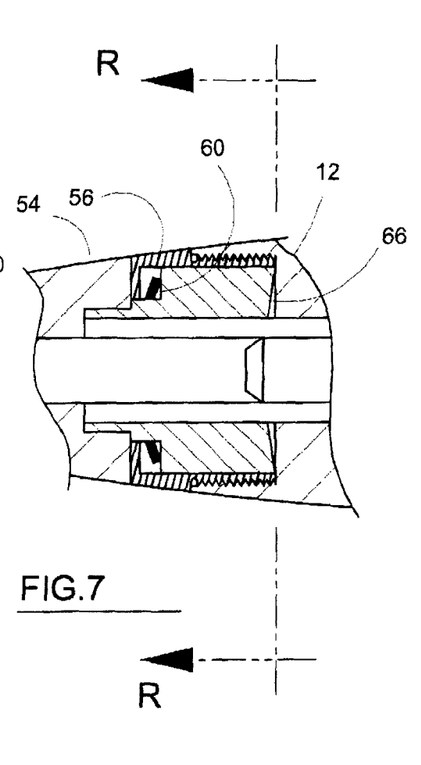
FIG. 7 is FIG. 6 enlarged sectional view shown in the closed or locked position.
Figure 8:
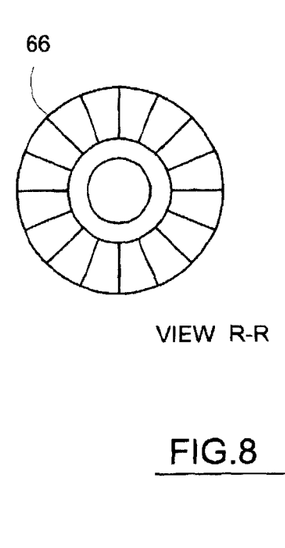
FIG. 8 is end view of the ratchet item 66 showing the 16 unique positions.
Figure 9:
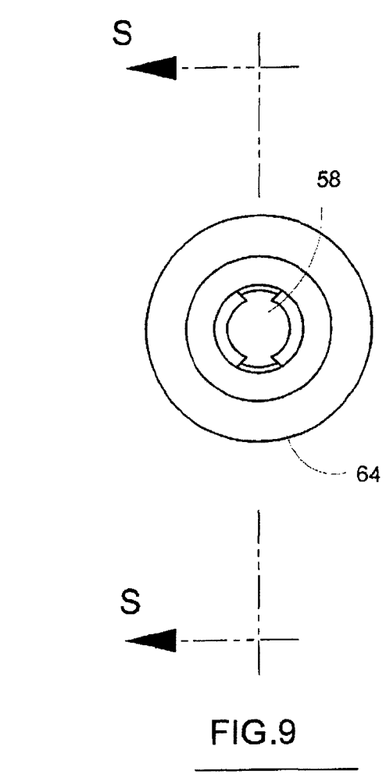
FIG. 9 is an end view of figure element 64 being the nose cone showing a quick disconnect area as element 58.
Figure 10:
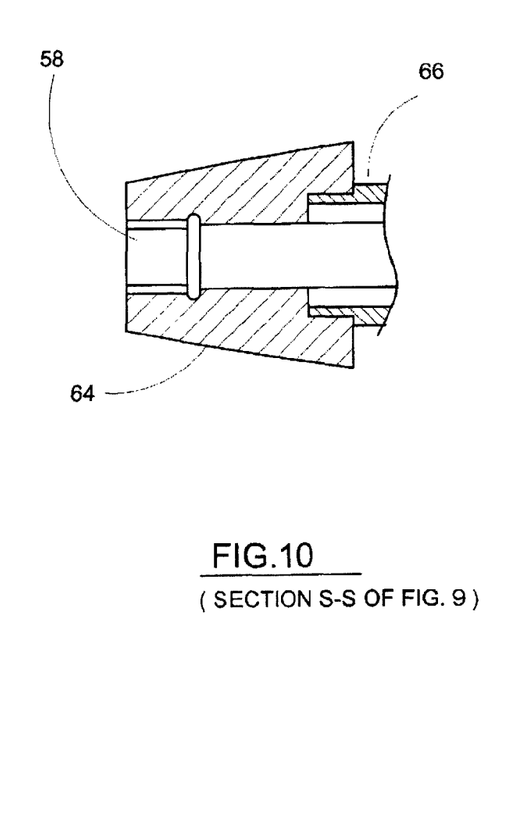
FIG. 10 is a partial sectional view of from FIG. 9.

Ratchet head 62 is constructed and arranged such that it rotates in a fixed number of incremental rotations such that the user can adjust the rotation of applicator tip 52 in a plurality of desired rotational positions. In one embodiment an applicator ratchet assembly 56 is incorporated in applicator assembly 50 and the ratchet mechanism regulates the control and desired rotation whereby the rotation is in fixed increments about the circumference of the circle. The rotation of the assembly is depicted by directional lines F and G of FIG. 7. In a preferred embodiment, applicant assembly 50 is connected to main body 12 of article 10 using a quick disconnect 58 whereby a connect/disconnect arrangement is possible with applicator tip 52 and main body 12.

Figures 11A, 13:
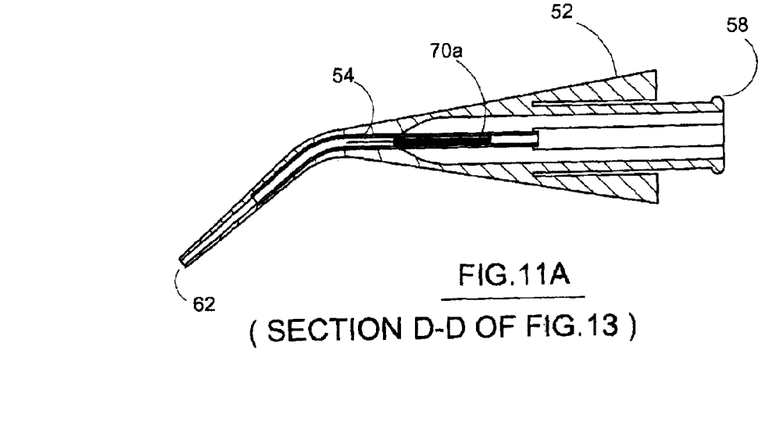
FIG. 13 is an end view of the applicator tip.
Figures 11B, 13:
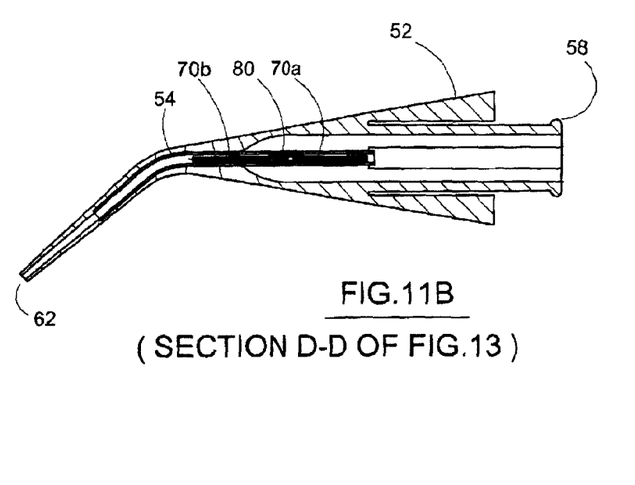

Although the FIG. 11A shows a single medicament dosage 70a within applicator tip 52 the present invention contemplates a plurality of doses contained therein. In one embodiment, shown in FIG. 11B, a precise first dose 70a is separated by a layer of a medically inert material 80 in order to avoid contact with of moisture with subsequent dose 70a.

Figure 14:
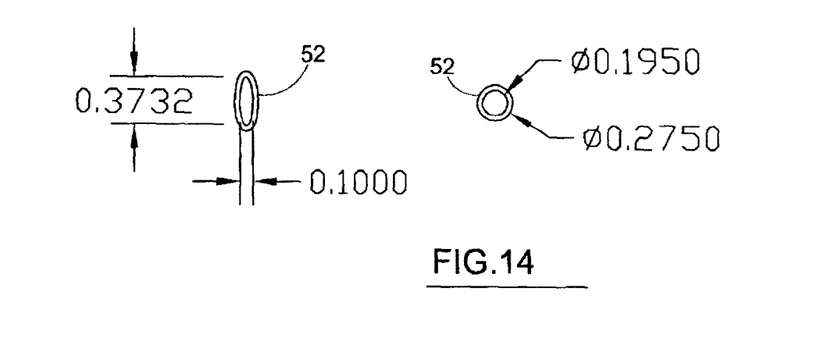
FIG. 14 is detail area of the applicator tips with different shapes but equal areas.
Figure 15:
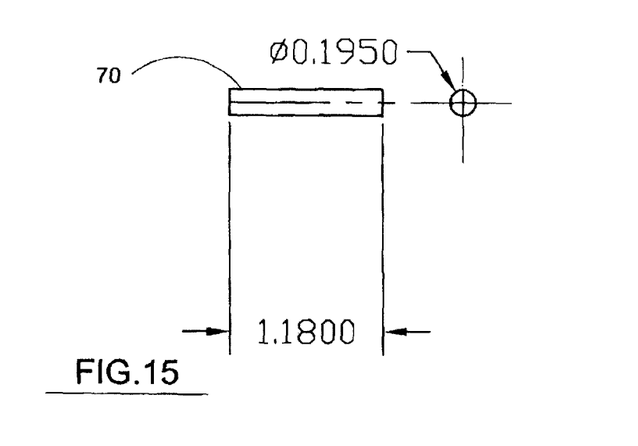
FIG. 15 is a detail of single powder shot item 70 with typical dimension.
Figure 16:
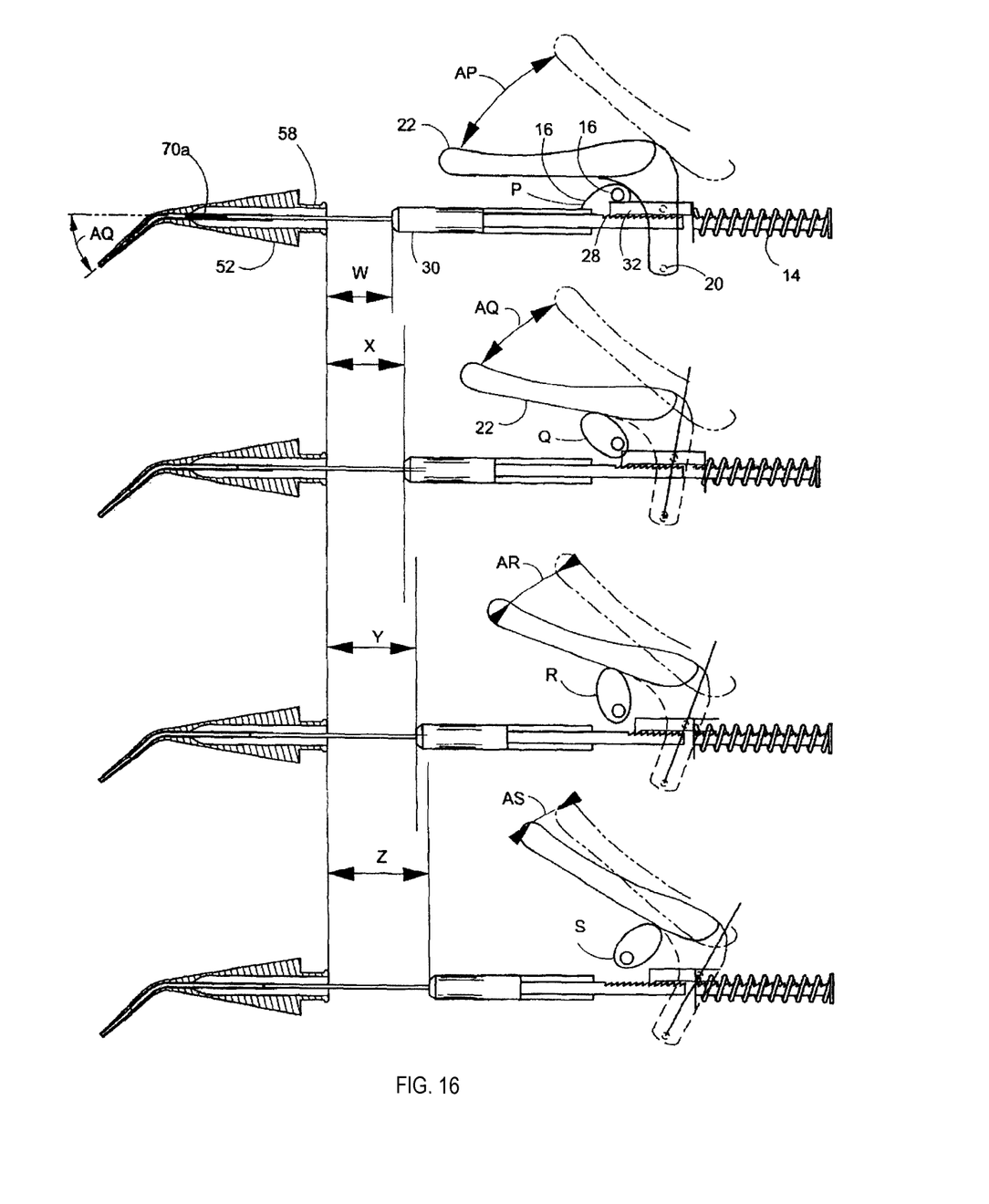
FIG. 16 is a series of views showing the various positions of the powder feed actuating mechanism whereby said mechanism can have a user-controlled tension.

As seen in FIGS. 14 and 15, the inner geometry whereby medicament travels for delivers can be altered without changing the cavity volume and adversely effect delivery precision. FIG. 14 demonstrates an oval configuration and FIG. 15 a generally circular configuration.

As best seen in FIG. 17, each of illustrated dimensions W, X, Y, and Z, represent a user adjustable distance whereby a conventional dose can be given at 100% dose amount represented by distance Z, or upon user adjustment, a precise percentage of a single dose is delivered. The delivery of an adjusted amount containing less than a 100% dose is delivered by adjusting the starting position of plunger 30 along rack 28 which interacts with pawl 32 and provides for fixed movement of plunger 30.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A hand-held device for dispensing multiple controlled dosage of powdered material comprising: a main body having a first end and a second end; a cavity, said cavity constructed and arranged to be operatively associated with an actuator for dispensing a powder medicament; an actuator constructed and arranged for dispensing said medicament from said cavity through a delivery device; a rotatable ratchet head which positionally rotates a tip assembly relative to the main body and actuator; a tip assembly comprising a blunt tip applicator constructed and arranged at a fixed angle relative to said main body to facilitate delivery of said medicament into a periodontal pocket; wherein said tip is pre-filled with more than one dose of powdered medicament, and each dose is separated from another dose by an inert material.

2. The device of claim 1 wherein said device is constructed and arranged to provide delivery of a plurality of doses of said medicament.

3. The device of claim 1 wherein said device provides pharmaceutically acceptable precision and uniformity to delivery of said medicament from said device.

4. The device of claim 1 wherein the force of delivery is user adjustable.

5. The device of claim 1 wherein said delivery device is formed as a regulated multi-dose applicator in the shape of a hollow thin conical elliptical shape at its apex, wherein said applicator is constructed having an approximately 10-degree to 50-degree angle offset from a longitudinal line through the center of the device.

* * * * *